United States Patent
Shen et al.

(10) Patent No.: US 10,448,879 B2
(45) Date of Patent: Oct. 22, 2019

(54) SKIN CONDITION DETECTION METHOD AND ELECTRONIC DEVICE

(71) Applicant: CAL-COMP BIG DATA, INC., New Taipei (TW)

(72) Inventors: Shyh-Yong Shen, New Taipei (TW); Min-Chang Chi, New Taipei (TW); Eric Budiman Gosno, New Taipei (TW); Ching-Wei Wang, New Taipei (TW)

(73) Assignee: CAL-COMP BIG DATA, INC., New Taipei (TW)

( * ) Notice: Subject to any disclaimer, the term of this patent is extended or adjusted under 35 U.S.C. 154(b) by 46 days.

(21) Appl. No.: 15/871,132

(22) Filed: Jan. 15, 2018

(65) Prior Publication Data
US 2019/0015037 A1    Jan. 17, 2019

(30) Foreign Application Priority Data
Jul. 14, 2017   (CN) .......................... 2017 1 0573087

(51) Int. Cl.
*G06K 9/00*   (2006.01)
*A61B 5/00*   (2006.01)
(Continued)

(52) U.S. Cl.
CPC ............ *A61B 5/442* (2013.01); *A61B 5/0077* (2013.01); *A61B 5/4842* (2013.01);
(Continued)

(58) Field of Classification Search
CPC combination set(s) only.
See application file for complete search history.

(56) References Cited

U.S. PATENT DOCUMENTS

| | | | | |
|---|---|---|---|---|
| 5,991,433 A | * | 11/1999 | Osanai | ............... G06K 9/00127 382/133 |
| 2003/0063801 A1 | * | 4/2003 | Rubinstenn | .......... A45D 44/005 382/190 |

(Continued)

FOREIGN PATENT DOCUMENTS

| | | |
|---|---|---|
| EP | 2178045 | 4/2010 |
| JP | H1043141 | 2/1998 |

(Continued)

OTHER PUBLICATIONS

"Search Report of Europe Counterpart Application", dated Oct. 16, 2018, p. 1-p. 10.

(Continued)

*Primary Examiner* — Alex Kok S Liew
(74) *Attorney, Agent, or Firm* — JCIPRNET

(57) ABSTRACT

A skin condition detection method and an electronic device are provided. The method includes: acquiring a first image; performing at least one skin condition detection on the first image to acquire at least one first characteristic value; acquiring at least one second characteristic value acquired through the skin condition detection in the second image; determining whether a skin condition in the first image has changed with respect to a skin condition in the second image according to the first characteristic value and the second characteristic value; and if the skin condition in the first image has changed with respect to the skin condition in the second image, outputting notification information to indicate that the skin condition in the first image has changed with respect to the skin condition in the second image. The invention makes it possible to effectively and clearly determine change of the skin condition.

14 Claims, 5 Drawing Sheets

(51) Int. Cl.
 *G06T 7/00* (2017.01)
 *G06T 7/60* (2017.01)
 *G16Z 99/00* (2019.01)
(52) U.S. Cl.
 CPC ........ *A61B 5/7282* (2013.01); *G06K 9/00221* (2013.01); *G06T 7/0016* (2013.01); *G06T 7/60* (2013.01); *G16Z 99/00* (2019.02); *A61B 2576/02* (2013.01); *G06T 2207/30041* (2013.01); *G06T 2207/30088* (2013.01); *G06T 2207/30201* (2013.01)

(56) References Cited

U.S. PATENT DOCUMENTS

| | | | |
|---|---|---|---|
| 2005/0197542 A1 | 9/2005 | Bazin et al. | |
| 2007/0064978 A1* | 3/2007 | Chhibber | G06K 9/00288 382/118 |
| 2007/0147708 A1* | 6/2007 | Lee | G06T 3/0012 382/298 |
| 2009/0155314 A1 | 6/2009 | Tezel et al. | |
| 2011/0116691 A1 | 5/2011 | Chung et al. | |
| 2015/0254851 A1* | 9/2015 | Daly | G06T 7/0016 382/128 |
| 2016/0143595 A1 | 5/2016 | Yoshida et al. | |

FOREIGN PATENT DOCUMENTS

| | | |
|---|---|---|
| JP | 2006081846 | 3/2006 |
| JP | 2006305184 | 11/2006 |
| JP | 2008029573 | 2/2008 |
| JP | 2010119431 | 6/2010 |
| JP | 2010148713 | 7/2010 |
| JP | 2013069122 | 4/2013 |
| JP | 2016022093 | 2/2016 |
| WO | 2014140926 | 9/2014 |
| WO | 2016076140 | 5/2016 |
| WO | 2016121518 | 8/2016 |

OTHER PUBLICATIONS

"Search Report of Europe Counterpart Application", dated Mar. 28, 2019, p. 1-p. 14.

Jhony K Pontes Et Al, "A flexible hierarchical approach for facial age estimation based on multiple features," Pattern Recognition, Elsevier, GB, vol. 54, Dec. 29, 2015, pp. 1-18.

Roh et al, "Treatment of Enlarged Pores with the Quasi Long-Pulsed Versus Q-Switched 1064nm Nd: YAG Lasers: A Split-Face, Comparative, Controlled Study," Laser Therapy, Sep. 22, 2011, pp. 1-p. 6.

"Office Action of Japan Counterpart Application," dated Apr. 23, 2019, p. 1-p. 12.

* cited by examiner

SKIN CONDITION DETECTION METHOD AND ELECTRONIC DEVICE

CROSS-REFERENCE TO RELATED APPLICATION

This application claims the priority benefit of Chinese application serial no. 201710573087.5, filed on Jul. 14, 2017. The entirety of the above-mentioned patent application is hereby incorporated by reference herein and made a part of this specification.

BACKGROUND

Field of the Invention

The invention relates to a skin condition detection method and an electronic device.

Description of Related Art

People grow older and their skin conditions usually change with time. The skin conditions refer to the number of wrinkles, the size of skin pores, or the degree of eye sagging, for example. However, people may not clearly know whether their skin conditions have changed. Therefore, how to effectively and clearly determine whether the skin conditions have changed is an issue that needs to be addressed in this field.

SUMMARY

The invention provides a skin condition detection method, adapted for determining whether a skin condition in face images has changed according to two face images that are captured at different time points, so as to output corresponding notification information.

The invention provides a skin condition detection method. The method includes: acquiring a first image; performing at least one skin condition detection on the first image to acquire at least one first characteristic value; acquiring at least one second characteristic value acquired through the skin condition detection in the second image; determining whether a skin condition in the first image has changed with respect to a skin condition in the second image according to the first characteristic value and the second characteristic value; and if the skin condition in the first image has changed with respect to the skin condition in the second image, outputting notification information to indicate that the skin condition in the first image has changed with respect to the skin condition in the second image.

The invention provides an electronic device. The electronic device includes a storage device and a processing device. The storage device is configured to store a plurality of modules. The processing device is coupled to the storage device and configured to access and execute the modules stored in the storage device, and the modules include an image acquisition module, a skin condition detection module, a characteristic value acquisition module, a skin condition determination module, and an output module. The image acquisition module acquires a first image. The skin condition detection module performs at least one skin condition detection on the first image to acquire at least one first characteristic value. The characteristic value acquisition module acquires at least one second characteristic value acquired through the skin condition detection in a second image. The skin condition determination module determines whether a skin condition in the first image has changed with respect to a skin condition in the second image according to the first characteristic value and the second characteristic value. If the skin condition in the first image has changed with respect to the skin condition in the second image, the output module outputs notification information to indicate that the skin condition in the first image has changed with respect to the skin condition in the second image.

Based on the above, the skin condition detection method of the invention is adapted for determining whether the skin condition in face images has changed according to two face images that are captured at different time points, so as to output the corresponding notification information. Accordingly, the user may more clearly know whether the skin condition in the current image has aged compared to the skin condition in the previous image.

In order to make the aforementioned and other features and advantages of the invention more comprehensible, several embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate exemplary embodiments of the invention and, together with the description, serve to explain the principles of the invention.

DESCRIPTION OF THE EMBODIMENTS

Figure 1:
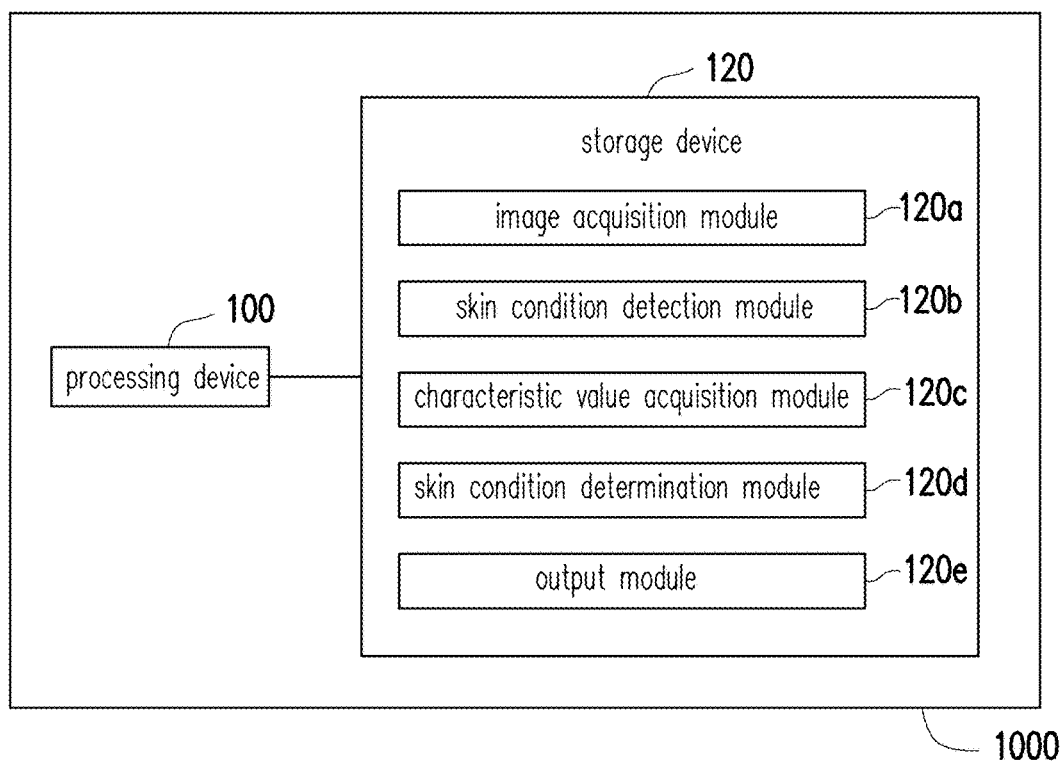
FIG. 1 is a block diagram showing an electronic device according to an embodiment of the invention.

FIG. 1 is a block diagram showing an electronic device according to an embodiment of the invention. Referring to FIG. 1, the electronic device 1000 includes a processing device 100 and a storage device 120. The processing device 100 is coupled to the storage device 120, but the invention is not limited thereto. In an embodiment of the invention, the electronic device 1000 may be a server, a smart mobile device, a desktop computer, a laptop computer, a workstation, a personal digital assistant (PDA), and so on, but the invention is not limited thereto.

The processing device 100 may be a central processing unit (CPU), a programmable microprocessor for general use or special use, a digital signal processor (DSP), a programmable controller, an application specific integrated circuit (ASIC), other similar devices, or a combination of the foregoing.

The storage device 120 may be any type of stationary or movable random access memory (RAM), read-only memory (ROM), flash memory, similar devices, or a combination of the foregoing.

In this exemplary embodiment, the storage device 120 of the electronic device 1000 stores a plurality of code snippets therein. The code snippets are executed by the processing device 100 after being installed. For example, the storage device 120 stores a plurality of modules, such as an image acquisition module 120a, a skin condition detection module 120b, a characteristic value acquisition module 120c, a skin condition determination module 120d, and an output module 120e, through which steps for the electronic device 1000 are executed respectively, wherein each of the modules is composed of one or more code snippets. It should be noted that the storage device 120 described in the above embodiment is not necessarily one single storage component, and the modules described above may be separately stored in two or more storage components of the same or different types. In some other embodiments of the invention, the modules may be implemented respectively by specific circuit structures.

In an embodiment of the invention, the electronic device 1000 further includes components, such as an input/output interface (not shown) and a communication interface (not shown), but the invention is not limited thereto. More specifically, the input/output interface includes components, such as a display, a loudspeaker, a keyboard, a mouse, a touch panel, and so on, for outputting or inputting information and data. In addition, the communication interface supports a variety of wired communication standards and wireless communication standards for the electronic device 1000 to connect with other devices.

A skin condition detection method provided in the embodiments of the invention is applicable to the electronic device 1000 shown in FIG. 1. Embodiments of the skin condition detection method are described in detail hereinafter with reference to the electronic device 1000 shown in FIG. 1. However, it should be noted that the skin condition detection method is not limited to being used on the electronic device 1000, and may also be used on other electronic devices or systems with corresponding capability.

Figure 2:
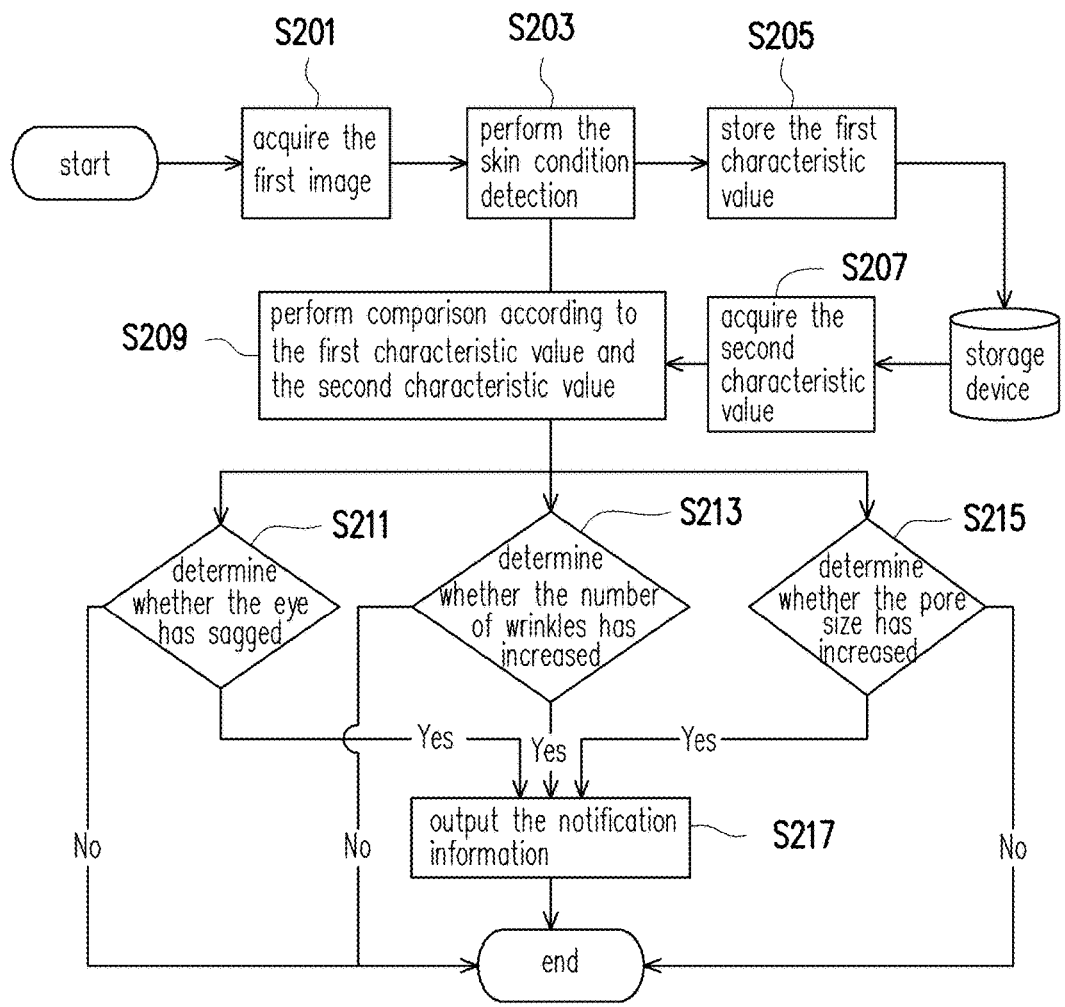
FIG. 2 is a flowchart showing a skin condition detection method according to an embodiment of the invention.

FIG. 2 is a flowchart showing the skin condition detection method according to an embodiment of the invention. Referring to FIG. 2, in Step S201, the image acquisition module 120a acquires a first image. The first image includes a face front area of a subject. The first image is captured and generated by the electronic device 1000 through an image acquisition device (not shown), for example. However, the invention is not intended to limit how the first image is acquired.

Then, in Step S203, the skin condition detection module 120b performs at least one skin condition detection on the first image to acquire at least one first characteristic value. The first characteristic value is a value used for determining the number of wrinkles, the size of skin pores, or the degree of eye sagging, for example. Details of the first characteristic value will be described later. Next, in Step S205, the skin condition detection module 120b stores the first characteristic value to the storage device 120. However, it should be noted that, in an exemplary embodiment, the skin condition detection module 120b may also store the first characteristic value to other databases or storage media, other than the storage device 120.

In Step S207, the characteristic value acquisition module 120c acquires at least one second characteristic value acquired through the skin condition detection described above in a second image from the storage device 120. In this exemplary embodiment, the subject in the second image is the same as the subject in the first image, and the second image also includes the face front area of the subject. In particular, a shooting time of the second image is earlier than a shooting time of the first image. For example, the shooting time of the second image is earlier than the shooting time of the first image by three months. Nevertheless, the invention is not intended to limit the time interval between the shooting time of the second image and the shooting time of the first image. Moreover, the second characteristic value of the second image is also acquired by executing the skin condition detection in Step S203 described above, for example, and the second characteristic value is stored in the storage device 120. However, it should be noted that, in an exemplary embodiment, the second characteristic value may also be stored in other databases or storage media, other than the storage device 120. The second characteristic value includes a value used for determining the number of wrinkles, the size of skin pores, or the degree of eye sagging, for example.

Thereafter, in Step S209, the skin condition determination module 120d compares the first characteristic value with the second characteristic value to determine whether a skin condition in the first image has changed with respect to a skin condition in the second image.

More specifically, in Step S211, the skin condition determination module 120d determines whether an eye in the first image has sagged with respect to an eye in the second image. In other words, the skin condition determination module 120d determines whether a height of the eye in the first image is lower than a height of the eye in the second image. If the eye in the first image has sagged with respect to the eye in the second image (i.e., if the height of the eye in the first image is lower than the height of the eye in the second image), in Step S217, the output module 120e outputs notification information to indicate that the eye in the first image has sagged with respect to the eye in the second image. In other words, the notification information is used to indicate that the degree of eye sagging in the first image is worse than the degree of eye sagging in the second image. If the eye in the first image does not sag with respect to the eye in the second image (i.e., if the height of the eye in the first image is greater than or equal to the height of the eye in the second image), the determination process of Step S211 is ended directly without outputting the notification information.

In addition, in Step S213, the skin condition determination module 120d determines whether the number of wrinkles of the subject in the first image has increased with respect to the number of wrinkles of the subject in the second image. If the number of wrinkles of the subject in the first image has increased with respect to the number of wrinkles of the subject in the second image (i.e., the number of wrinkles in the first image is more than the number of wrinkles in the second image), in Step S217, the output module 120e outputs the notification information to indicate that the number of wrinkles in the first image has increased with respect to the number of wrinkles in the second image. In other words, the notification information is used to indicate that the number of wrinkles in the first image is more than the number of wrinkles in the second image. If the number of wrinkles of the subject in the first image does not increase with respect to the number of wrinkles of the subject in the second image (i.e., if the number of wrinkles in the first image is smaller than or equal to the number of wrinkles in the second image), the determination process of Step S213 is ended directly without outputting the notification information.

Further, in Step S215, the skin condition determination module 120d determines whether a pore size of the subject in the first image has increased with respect to a pore size of the subject in the second image. If the pore size of the subject in the first image has increased with respect to the pore size of the subject in the second image (i.e., if the pore size in the first image is larger than the pore size in the second image), in Step S217, the output module 120e outputs the notification information to indicate that the pore size in the first image has increased with respect to the pore size of the subject in the second image. In other words, the notification information is used to indicate that the pore size in the first image is larger than the pore size in the second image. If the pore size of the subject in the first image does not increase with respect to the pore size of the subject in the second image (i.e., if the pore size in the first image is smaller than or equal to the pore size in the second image), the determination process of Step S215 is ended directly without outputting the notification information.

Several embodiments are provided hereinafter to explain in detail how to determine whether the skin condition (e.g., the degree of eye sagging, the number of wrinkles, and the pore size) in the first image has changed with respect to the skin condition in the second image according to the first characteristic value and the second characteristic value.

Figure 3:
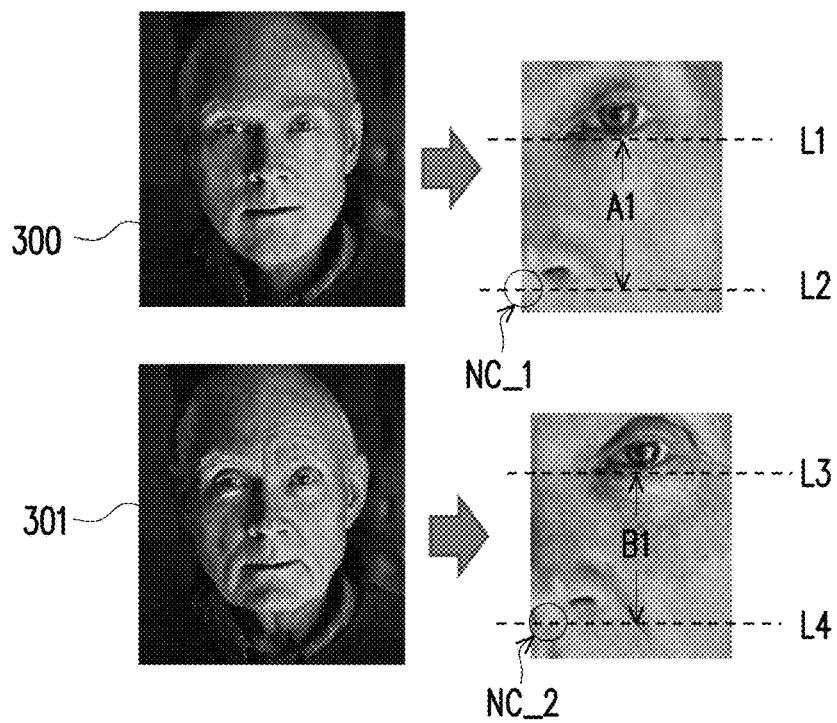
FIG. 3 illustrates how to determine whether the eye has sagged according to an embodiment of the invention.

FIG. 3 illustrates how to determine whether the eye has sagged according to an embodiment of the invention. Referring to FIG. 3, here it is assumed that an image 300 is the second image described above and an image 301 is the first image described above, and the shooting time of the image 300 is earlier than the shooting time of the image 301. When the image acquisition module 120a acquires the image 300, the skin condition detection module 120b may perform the skin condition detection on the image 300 to acquire the height of the eye. More specifically, the skin condition detection module 120b acquires a vertical distance A1 (also referred to as "second vertical distance") between a horizontal line L1 (also referred to as "third horizontal line"), which passes through the lower edge of the eye, and a horizontal line L2 (also referred to as "fourth horizontal line"), which passes through a nasal columella NC_1, in the image 300. Then, the electronic device 1000 may store the vertical distance A1 to the storage device 120 through the skin condition detection module 120b for subsequent comparison, for example. In other words, the second characteristic value described above may include this characteristic distance A1.

It is assumed that a certain period of time (e.g., three months) has passed, and when the image acquisition module 120a acquires the image 301, the skin condition detection module 120b further acquires a vertical distance B1 (also referred to as "first vertical distance") between a horizontal line L3 (also referred to as "first horizontal line"), which passes through the lower edge of the eye, and a horizontal line L4 (also referred to as "second horizontal line"), which passes through a nasal columella NC_2, in the image 301. The electronic device 1000 may also store the vertical distance B1 to the storage device 120 through the skin condition detection module 120b, for example. In particular, the first characteristic value described above may include this characteristic distance B1.

After the skin condition detection module 120b acquires the vertical distance B1 of the image 301, the vertical distance A1 of the image 300 previously stored in the storage device 120 (e.g., three months ago) may be acquired through the characteristic value acquisition module 120c. The skin condition determination module 120d determines whether a difference obtained by subtracting the vertical distance B1 from the vertical distance A1 is greater than a first threshold value. If the difference obtained by subtracting the vertical distance B1 from the vertical distance A1 is greater than the first threshold value, the output module 120e may output the notification information to indicate that the eye in the image 301 has sagged with respect to the eye in the previous image 300. Moreover, if the difference obtained by subtracting the vertical distance B1 from the vertical distance A1 is smaller than or equal to the first threshold value, it indicates that the eye sagging of the subject is less severe and the output module 120e may not output the notification information. In particular, the invention is not intended to limit the value of the first threshold value, and the invention is not intended to limit the notification information to a certain type, either.

Accordingly, the invention makes it possible to effectively determine whether the eye of the subject in the current image has sagged with respect to the eye in the previously captured image.

Figure 4:
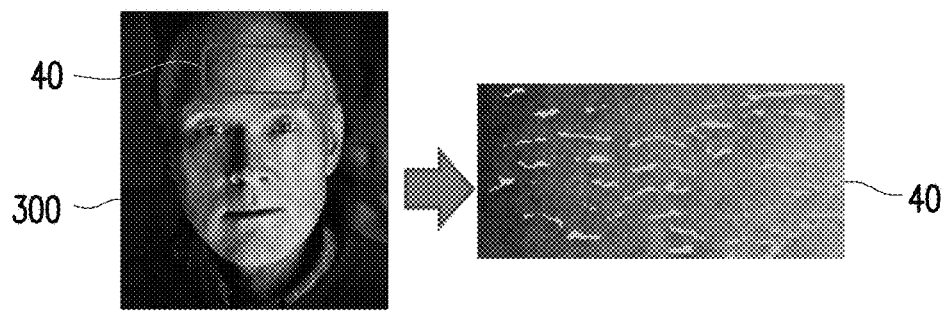
FIG. 4 illustrates how to determine whether the number of wrinkles has increased according to an embodiment of the invention.
Figure 4:
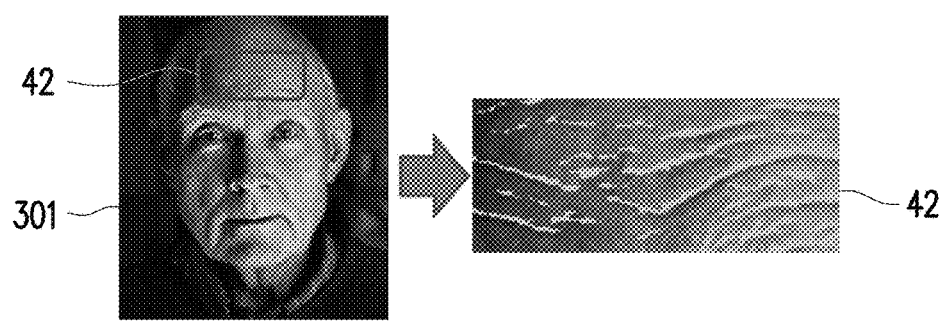

FIG. 4 illustrates how to determine whether the number of wrinkles has increased according to an embodiment of the invention. Referring to FIG. 4, the following is described based on the image 300 and the image 301 of FIG. 3, and the shooting time of the image 300 is earlier than the shooting time of the image 301.

When the image acquisition module 120a acquires the image 300, the skin condition detection module 120b may perform the skin condition detection on the image 300 to acquire the number of wrinkles. More specifically, the skin condition detection module 120b calculates and acquires a wrinkle percentage (also referred to as "second wrinkle percentage") of a forehead area 40 in the image 300. The second wrinkle percentage indicates the percentage of wrinkles in the forehead area 40. Then, the electronic device 1000 may store the second wrinkle percentage to the storage device 120 through the skin condition detection module 120b for subsequent comparison, for example. In other words, the second characteristic value described above may include the wrinkle percentage of the forehead area 40 in the image 300. In particular, the number or percentage of the wrinkles in the image may be calculated by an existing method and thus will not be repeated hereinafter.

It is assumed that a certain period of time (e.g., three months) has passed, and when the image acquisition module 120a acquires the image 301, the skin condition detection module 120b further acquires a wrinkle percentage (also referred to as "first wrinkle percentage") of a forehead area 42 in the image 301. The first wrinkle percentage indicates the percentage of wrinkles in the forehead area 42. The electronic device 1000 may also store the first wrinkle percentage to the storage device 120 through the skin condition detection module 120b, for example. In particular, the first characteristic value described above may include the wrinkle percentage of the forehead area 42 in the image 301.

After the skin condition detection module 120b acquires the first wrinkle percentage of the image 301, the second wrinkle percentage of the image 300 previously stored in the storage device 120 (e.g., three months ago) may be acquired through the characteristic value acquisition module 120c. The skin condition determination module 120d determines whether a difference obtained by subtracting the second wrinkle percentage from the first wrinkle percentage is greater than a threshold value (also referred to as "second threshold value"). If the difference obtained by subtracting the second wrinkle percentage from the first wrinkle percentage is greater than the second threshold value, the output module 120e outputs the notification information to indicate that the number of wrinkles in the image 301 has increased with respect to the number of wrinkles in the image 300. Moreover, if the difference obtained by subtracting the second wrinkle percentage from the first wrinkle percentage is smaller than or equal to the second threshold value, it indicates that the increase of the wrinkles of the subject is less severe and the output module 120e may not output the notification information. In particular, the invention is not intended to limit the value of the second threshold value, and the invention is not intended to limit the notification information to a certain type, either.

Figure 5:
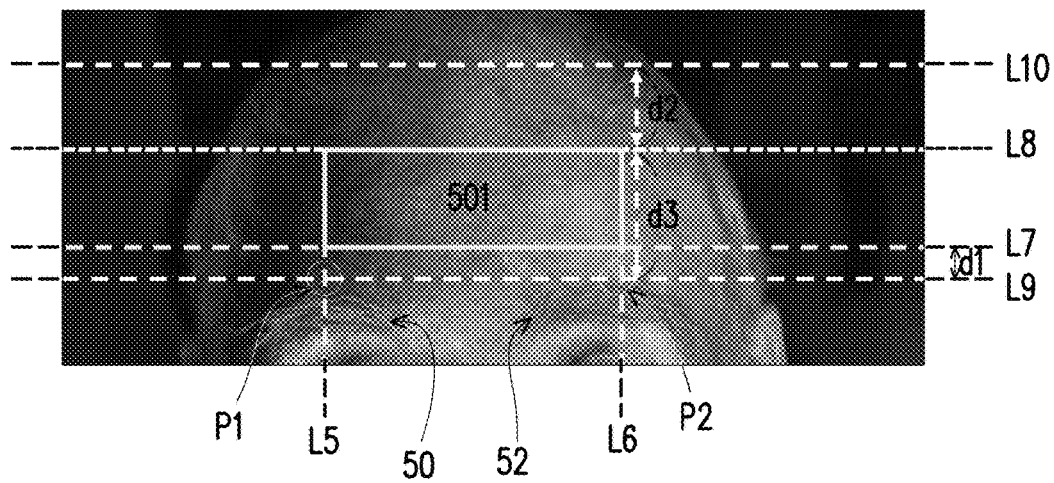
FIG. 5 illustrates an image of a forehead area acquired according to an embodiment of the invention.

It should be noted that FIG. 5 illustrates an image of the forehead area acquired according to an embodiment of the invention. Referring to FIG. 5, the forehead areas in the image 300 and the image 301 of FIG. 4 may be defined according to the embodiment of FIG. 5, for example. Take an image 500 in FIG. 5 as an example, a forehead area 501 of the image 500 may be defined by a vertical line L5 (also referred to as "first vertical line") passing through a center point P1 of the upper edge of an eyebrow 50, a vertical line L6 (also referred to as "second vertical line") passing through a center point P2 of the upper edge of an eyebrow 52, a horizontal line L7 (also referred to as "fifth horizontal line"), and a horizontal line L8 (also referred to as "sixth horizontal line"). The horizontal line L7 is spaced from a horizontal line L9 (also referred to as "seventh horizontal line") passing through the upper edges of the eyebrow 50 and the eyebrow 52 by a distance d1 (also referred to as "first distance"), the horizontal line L8 is spaced from a horizontal line L10 (also referred to as "eighth horizontal line") passing through a hairline by a distance d2 (also referred to as "second distance"), and the horizontal line L8 is spaced from the horizontal line L9 by a distance d3 (also referred to as "third distance"). The distance d1 is 50 primitives, for example, and a ratio of the distance d2 to the distance d3 is 1 to 2. However, it should be noted that the invention is not intended to limit the ratios among the distance d1, the distance d2, and the distance d3, and their respective values.

Accordingly, the forehead areas of the faces in the image 300 and the image 301 may be acquired effectively, and the first wrinkle percentage and the second wrinkle percentage may be calculated for the acquired forehead areas respectively, so as to determine whether the number of wrinkles in the image 301 has increased with respect to the number of wrinkles in the image 300 according to the first wrinkle percentage and the second wrinkle percentage.

Figure 6:
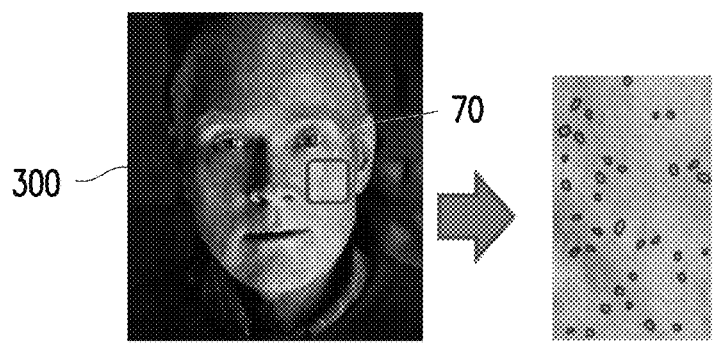
FIG. 6 illustrates how to determine whether a pore size has increased according to an embodiment of the invention.
Figure 6:
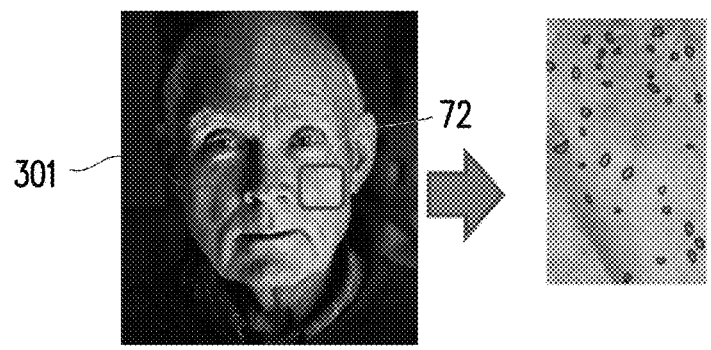

FIG. 6 illustrates how to determine whether the pore size has increased according to an embodiment of the invention. Referring to FIG. 6, the following is described based on the image 300 and the image 301 of FIG. 3, and the shooting time of the image 300 is earlier than the shooting time of the image 301.

When the image acquisition module 120a acquires the image 300, the skin condition detection module 120b may perform the skin condition detection on the image 300 to acquire an average value of the pore sizes in the image 300. More specifically, the skin condition detection module 120b calculates and acquires a pore size average value (also referred to as "second pore size average value") of a cheek area 70 in the image 300. The second pore size average value indicates the average size of all the pores in the cheek area 70. Then, the electronic device 1000 may store the second pore size average value to the storage device 120 through the skin condition detection module 120b for subsequent comparison, for example. In other words, the second characteristic value described above may include the pore size average value of the cheek area 70 in the image 300. In particular, the size of the pore in the image and the average value of the pore sizes may be calculated by an existing method and thus will not be repeated hereinafter.

It is assumed that a certain period of time (e.g., three months) has passed, and when the image acquisition module 120a acquires the image 301, the skin condition detection module 120b also acquires a pore size average value (also referred to as "first pore size average value") of a cheek area 72 in the image 301. The electronic device 1000 may also store the first pore size average value to the storage device 120 through the skin condition detection module 120b, for example. In particular, the first characteristic value described above may include the first pore size average value of the cheek area 72 in the image 301.

After the skin condition detection module 120b acquires the first pore size average value of the image 301, the second pore size average value of the image 300 previously stored in the storage device 120 (e.g., three months ago) may be acquired through the characteristic value acquisition module 120c. The skin condition determination module 120d determines whether a difference obtained by subtracting the second pore size average value from the first pore size average value is greater than a threshold value (also referred to as "third threshold value"). If the difference obtained by subtracting the second pore size average value from the first pore size average value is greater than the third threshold value, the output module 120e outputs the notification information to indicate that the pore size in the image 301 has increased with respect to the pore size in the image 300. Moreover, if the difference obtained by subtracting the second pore size average value from the first pore size average value is smaller than or equal to the third threshold value, it indicates that the increase of the pore size of the subject is less severe and the output module 120e may not output the notification information. In particular, the invention is not intended to limit the value of the third threshold value, and the invention is not intended to limit the notification information to a certain type, either.

Figure 7:
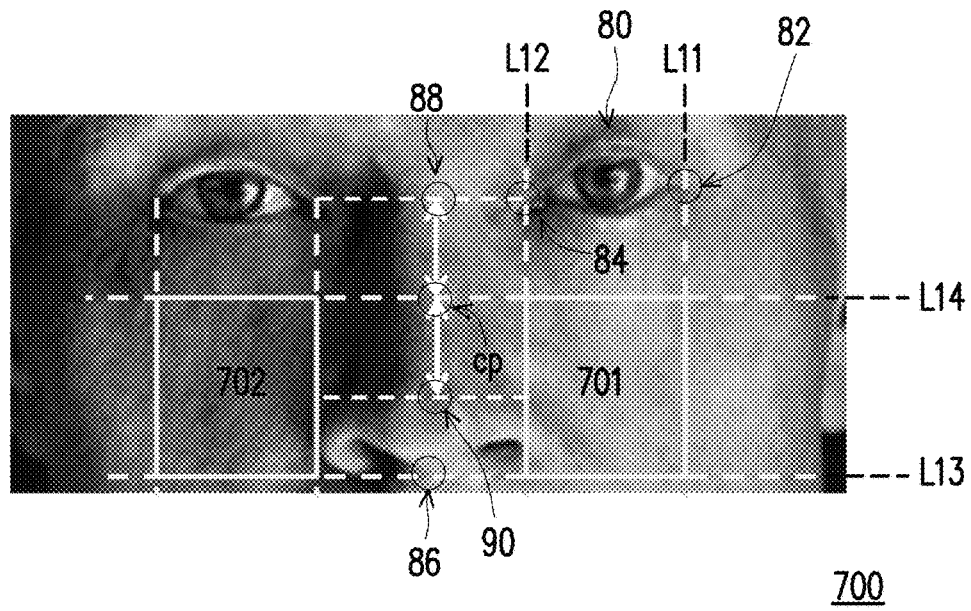
FIG. 7 illustrates an image of a cheek area acquired according to an embodiment of the invention.

It should be noted that FIG. 7 illustrates an image of the cheek area acquired according to an embodiment of the invention. Referring to FIG. 7, the cheek areas in the image 300 and the image 301 of FIG. 6 may be defined according to the embodiment of FIG. 7, for example. Take an image 700 in FIG. 7 as an example, a cheek area 701 of the image 700 may be defined by a vertical line L11 (also referred to as "third vertical line") passing through a canthus 82 of an eye 80, a vertical line L12 (also referred to as "fourth vertical line") passing through a canthus 84 of the eye 80, a horizontal line L13 (also referred to as "ninth horizontal line") passing through a nasal columella 86, and another horizontal line L14 (also referred to as "tenth horizontal line"), wherein the horizontal line L14 passes through a center point cp between a nose bridge 88 and a nose tip 90. In addition, the cheek area 702 may also be acquired by a method similar to that described above and thus is not repeated hereinafter.

Accordingly, the cheek areas of the faces in the image 300 and the image 301 may be acquired effectively, and the first pore size average value and the second pore size average value may be calculated for the acquired cheek areas respectively, so as to determine whether the pore size in the image 301 has increased with respect to the pore size in the image 300 according to the first pore size average value and the second pore size average value.

Figure 8:
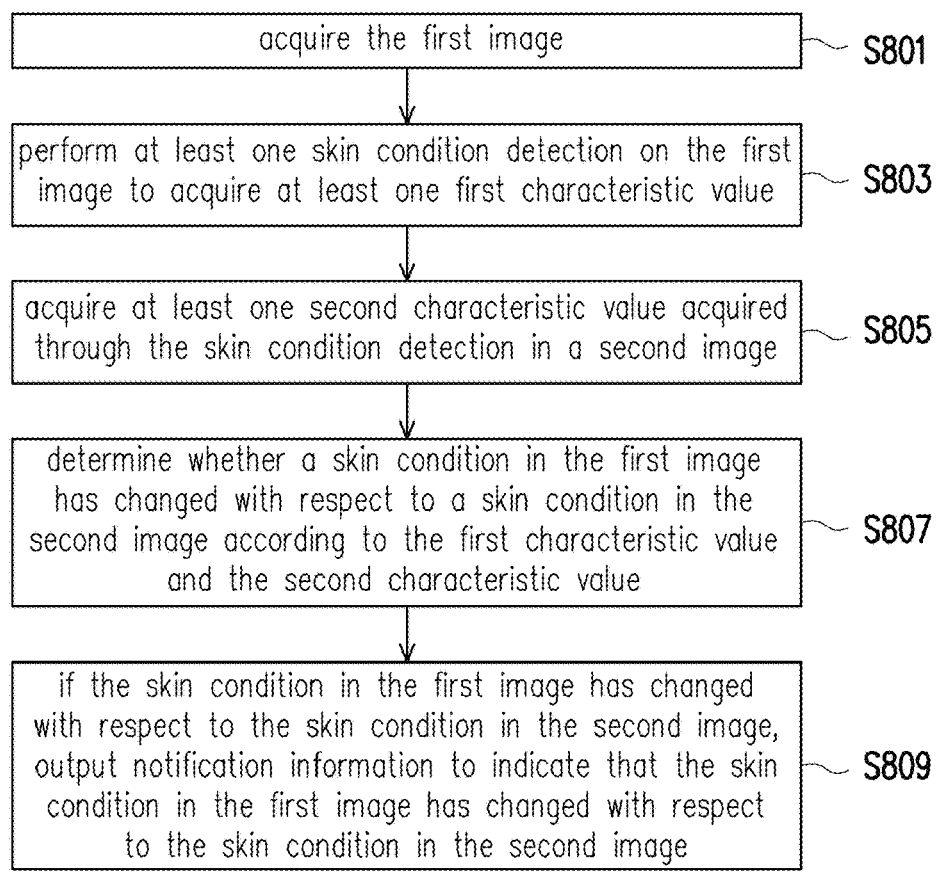
FIG. 8 is a flowchart showing a skin condition detection method according to an embodiment of the invention.

FIG. 8 is a flowchart showing a skin condition detection method according to an embodiment of the invention.

Referring to FIG. 8, in Step S801, the image acquisition module 120a acquires a first image. In Step S803, the skin condition detection module 120b performs at least one skin condition detection on the first image to acquire at least one first characteristic value. In Step S805, the characteristic value acquisition module 120c acquires at least one second characteristic value acquired through the skin condition detection in a second image. In Step S807, the skin condition determination module 120d determines whether the skin condition in the first image has changed with respect to the skin condition in the second image according to the first characteristic value and the second characteristic value. If the skin condition in the first image has changed with respect to the skin condition in the second image, in Step S809, the output module 120e outputs notification information to indicate that the skin condition in the first image has changed with respect to the skin condition in the second image.

To sum up, the skin condition detection method of the invention is adapted for determining whether the skin condition in face images has changed according to two face images that are captured at different time points, so as to output the corresponding notification information. Accordingly, the user may more clearly know whether the skin condition in the current image has aged compared to the skin condition in the previous image.

It will be apparent to those skilled in the art that various modifications and variations can be made to the disclosed embodiments without departing from the scope or spirit of the invention. In view of the foregoing, it is intended that the invention covers modifications and variations of this disclosure provided that they fall within the scope of the following claims and their equivalents.

What is claimed is:

1. A skin condition detection method, comprising:
   acquiring a first image;
   performing at least one skin condition detection on the first image to acquire at least one first characteristic value;
   acquiring at least one second characteristic value acquired through the at least one skin condition detection in a second image;
   determining whether a skin condition in the first image has changed with respect to a skin condition in the second image according to the at least one first characteristic value and the at least one second characteristic value; and
   outputting notification information to indicate that the skin condition in the first image has changed with respect to the skin condition in the second image if the skin condition in the first image has changed with respect to the skin condition in the second image,
   wherein performing the at least one skin condition detection on the first image to acquire the at least one first characteristic value comprises:
   acquiring a first vertical distance between a first horizontal line passing through a lower edge of an eye and a second horizontal line passing through a nasal columella in the first image,
   wherein acquiring the at least one second characteristic value acquired through the at least one skin condition detection in the second image comprises:
   acquiring a second vertical distance between a third horizontal line passing through a lower edge of an eye and a fourth horizontal line passing through a nasal columella in the second image.

2. The skin condition detection method according to claim 1, wherein determining whether the skin condition in the first image has changed with respect to the skin condition in the second image comprises:
   determining whether a difference obtained by subtracting the first vertical distance from the second vertical distance is greater than a first threshold value,
   wherein outputting the notification information to indicate that the skin condition in the first image has changed with respect to the skin condition in the second image if the skin condition in the first image has changed with respect to the skin condition in the second image comprises:
   outputting the notification information to indicate that the eye in the first image has sagged with respect to the eye in the second image if the difference obtained by subtracting the first vertical distance from the second vertical distance is greater than the first threshold value.

3. A skin condition detection method, comprising:
   acquiring a first image;
   performing at least one skin condition detection on the first image to acquire at least one first characteristic value;
   acquiring at least one second characteristic value acquired through the at least one skin condition detection in a second image;
   determining whether a skin condition in the first image has changed with respect to a skin condition in the second image according to the at least one first characteristic value and the at least one second characteristic value; and
   outputting notification information to indicate that the skin condition in the first image has changed with respect to the skin condition in the second image if the skin condition in the first image has changed with respect to the skin condition in the second image,
   wherein performing the at least one skin condition detection on the first image to acquire the at least one first characteristic value comprises:
   acquiring a first wrinkle percentage of a forehead area in the first image,
   wherein acquiring the at least one second characteristic value acquired through the at least one skin condition detection in the second image comprises:
   acquiring a second wrinkle percentage of a forehead area in the second image,
   wherein determining whether the skin condition in the first image has changed with respect to the skin condition in the second image comprises:
   determining whether a difference obtained by subtracting the second wrinkle percentage from the first wrinkle percentage is greater than a second threshold value,
   wherein outputting the notification information to indicate that the skin condition in the first image has changed with respect to the skin condition in the second image if the skin condition in the first image has changed with respect to the skin condition in the second image comprises:
   outputting the notification information to indicate that the number of wrinkles in the first image has increased with respect to the number of wrinkles in the second image if the difference obtained by subtracting the second wrinkle percentage from the first wrinkle percentage is greater than the second threshold value.

4. The skin condition detection method according to claim 3, wherein the forehead areas in the first image and the second image are defined by a first vertical line passing through a center point of an eyebrow, a second vertical line passing through a center point of another eyebrow, a fifth horizontal line, and a sixth horizontal line, wherein the fifth horizontal line is spaced from a seventh horizontal line passing through upper edges of the eyebrow and the another eyebrow by a first distance, the sixth horizontal line is spaced from an eighth horizontal line passing through a hairline by a second distance, and the sixth horizontal line is spaced from the seventh horizontal line by a third distance.

5. The skin condition detection method according to claim 4, wherein a ratio of the second distance to the third distance is 1 to 2.

6. A skin condition detection method, comprising:
acquiring a first image;
performing at least one skin condition detection on the first image to acquire at least one first characteristic value;
acquiring at least one second characteristic value acquired through the at least one skin condition detection in a second image;
determining whether a skin condition in the first image has changed with respect to a skin condition in the second image according to the at least one first characteristic value and the at least one second characteristic value; and
outputting notification information to indicate that the skin condition in the first image has changed with respect to the skin condition in the second image if the skin condition in the first image has changed with respect to the skin condition in the second image,
wherein performing the at least one skin condition detection on the first image to acquire the at least one first characteristic value comprises:
acquiring a first pore size average value of a cheek area in the first image,
wherein acquiring the at least one second characteristic value acquired through the at least one skin condition detection in the second image comprises:
acquiring a second pore size average value of a cheek area in the second image,
wherein determining whether the skin condition in the first image has changed with respect to the skin condition in the second image comprises:
determining whether a difference obtained by subtracting the second pore size average value from the first pore size average value is greater than a third threshold value,
wherein outputting the notification information to indicate that the skin condition in the first image has changed with respect to the skin condition in the second image if the skin condition in the first image has changed with respect to the skin condition in the second image comprises:
outputting the notification information to indicate that a pore size in the first image has increased with respect to a pore size in the second image if the difference obtained by subtracting the second pore size average value from the first pore size average value is greater than the third threshold value.

7. The skin condition detection method according to claim 6, wherein the cheek areas in the first image and the second image are defined by a third vertical line passing through a canthus of an eye, a fourth vertical line passing through another canthus of the eye, a ninth horizontal line passing through a nasal columella, and a tenth horizontal line, wherein the tenth horizontal line passes through a center point between a nose bridge and a nose tip.

8. An electronic device, comprising:
a storage device configured to store a plurality of modules; and
a processing device coupled to the storage device and configured to access and execute the modules stored in the storage device to perform the following operations:
acquiring a first image;
performing at least one skin condition detection on the first image to acquire at least one first characteristic value;
acquiring at least one second characteristic value acquired through the at least one skin condition detection in a second image;
determining whether a skin condition in the first image has changed with respect to a skin condition in the second image according to the at least one first characteristic value and the at least one second characteristic value; and
outputting notification information to indicate that the skin condition in the first image has changed with respect to the skin condition in the second image if the skin condition in the first image has changed with respect to the skin condition in the second image,
wherein when performing the at least one skin condition detection on the first image to acquire the at least one first characteristic value,
the processing device acquires a first vertical distance between a first horizontal line passing through a lower edge of an eye and a second horizontal line passing through a nasal columella in the first image,
wherein when acquiring the at least one second characteristic value acquired through the at least one skin condition detection in the second image,
the processing device acquires a second vertical distance between a third horizontal line passing through a lower edge of an eye and a fourth horizontal line passing through a nasal columella in the second image.

9. The electronic device according to claim 8, wherein when determining whether the skin condition in the first image has changed with respect to the skin condition in the second image,
the processing device determines whether a difference obtained by subtracting the first vertical distance from the second vertical distance is greater than a first threshold value,
wherein when outputting the notification information to indicate that the skin condition in the first image has changed with respect to the skin condition in the second image if the skin condition in the first image has changed with respect to the skin condition in the second image,
the processing device outputs the notification information to indicate that the eye in the first image has sagged with respect to the eye in the second image if the difference obtained by subtracting the first vertical distance from the second vertical distance is greater than the first threshold value.

10. An electronic device, comprising:
a storage device configured to store a plurality of modules; and
a processing device coupled to the storage device and configured to access and execute the modules stored in the storage device to perform the following operations:
acquiring a first image;

performing at least one skin condition detection on the first image to acquire at least one first characteristic value;

acquiring at least one second characteristic value acquired through the at least one skin condition detection in a second image;

determining whether a skin condition in the first image has changed with respect to a skin condition in the second image according to the at least one first characteristic value and the at least one second characteristic value; and outputting notification information to indicate that the skin condition in the first image has changed with respect to the skin condition in the second image if the skin condition in the first image has changed with respect to the skin condition in the second image, wherein when performing the at least one skin condition detection on the first image to acquire the at least one first characteristic value, the processing device acquires a first wrinkle percentage of a forehead area in the first image, wherein when acquiring the at least one second characteristic value acquired through the at least one skin condition detection in the second image, the processing device acquires a second wrinkle percentage of a forehead area in the second image, wherein when determining whether the skin condition in the first image has changed with respect to the skin condition in the second image, the processing device determines whether a difference obtained by subtracting the second wrinkle percentage from the first wrinkle percentage is greater than a second threshold value, wherein when outputting the notification information to indicate that the skin condition in the first image has changed with respect to the skin condition in the second image if the skin condition in the first image has changed with respect to the skin condition in the second image, the processing device outputs the notification information to indicate that the number of wrinkles in the first image has increased with respect to the number of wrinkles in the second image if the difference obtained by subtracting the second wrinkle percentage from the first wrinkle percentage is greater than the second threshold value.

11. The electronic device according to claim 10, wherein the forehead areas in the first image and the second image are defined by a first vertical line passing through a center point of an eyebrow, a second vertical line passing through a center point of another eyebrow, a fifth horizontal line, and a sixth horizontal line, wherein the fifth horizontal line is spaced from a seventh horizontal line passing through upper edges the eyebrow and the another eyebrow by a first distance, the sixth horizontal line is spaced from an eighth horizontal line passing through a hairline by a second distance, and the sixth horizontal line is spaced from the seventh horizontal line by a third distance.

12. The electronic device according to claim 11, wherein a ratio of the second distance to the third distance is 1 to 2.

13. An electronic device, comprising:
a storage device configured to store a plurality of modules; and
a processing device coupled to the storage device and configured to access and execute the modules stored in the storage device to perform the following operations:
acquiring a first image;
performing at least one skin condition detection on the first image to acquire at least one first characteristic value;
acquiring at least one second characteristic value acquired through the at least one skin condition detection in a second image;
determining whether a skin condition in the first image has changed with respect to a skin condition in the second image according to the at least one first characteristic value and the at least one second characteristic value; and
outputting notification information to indicate that the skin condition in the first image has changed with respect to the skin condition in the second image if the skin condition in the first image has changed with respect to the skin condition in the second image, wherein when performing the at least one skin condition detection on the first image to acquire the at least one first characteristic value, the processing device acquires a first pore size average value of a cheek area in the first image, wherein when acquiring the at least one second characteristic value acquired through the at least one skin condition detection in the second image, the processing device acquires a second pore size average value of a cheek area in the second image, wherein when determining whether the skin condition in the first image has changed with respect to the skin condition in the second image, the processing device determines whether a difference obtained by subtracting the second pore size average value from the first pore size average value is greater than a third threshold value, wherein when outputting the notification information to indicate that the skin condition in the first image has changed with respect to the skin condition in the second image if the skin condition in the first image has changed with respect to the skin condition in the second image, the processing device outputs the notification information to indicate that a pore size in the first image has increased with respect to a pore size in the second image if the difference obtained by subtracting the second pore size average value from the first pore size average value is greater than the third threshold value.

14. The electronic device according to claim 13, wherein the cheek areas in the first image and the second image are defined by a third vertical line passing through a canthus of an eye, a fourth vertical line passing through another canthus of the eye, a ninth horizontal line passing through a nasal columella, and a tenth horizontal line, wherein the tenth horizontal line passes through a center point between a nose bridge and a nose tip.

* * * * *